United States Patent [19]

Pederson et al.

[11] Patent Number: 5,220,007
[45] Date of Patent: Jun. 15, 1993

[54] METHOD OF SITE-SPECIFIC ALTERATION OF RNA AND PRODUCTION OF ENCODED POLYPEPTIDES

[75] Inventors: Thoru Pederson, Worcester; Sudhir Agrawal, Shrewsbury; Sandra Mayrand, Shrewsbury; Paul C. Zamecnik, Shrewsbury, all of Mass.

[73] Assignee: The Worcester Foundation for Experimental Biology, Shrewsbury, Mass.

[21] Appl. No.: 839,472

[22] Filed: Feb. 19, 1992

Related U.S. Application Data

[63] Continuation of Ser. No. 480,269, Feb. 15, 1990, Pat. No. 5,149,797.

[51] Int. Cl.$^5$ .................. C12N 15/11; C07H 21/04
[52] U.S. Cl. .................... 536/23.1; 536/25.7; 536/22.1; 536/23.5; 935/2; 935/8; 935/36
[58] Field of Search .................. 536/27, 28, 29

[56] References Cited

U.S. PATENT DOCUMENTS 5,013,830  5/1991  Ohtsuka et al. .................. 536/27

FOREIGN PATENT DOCUMENTS

WO90/15065  12/1990  PCT Int'l Appl. .................. 435/27

OTHER PUBLICATIONS

Walder, R. Y., et al., 1988, Proceedings of the National Academy of Sciences, USA, 85: 5011-5015.
Fardon, P. J., et al., 1989, Nucleic Acids Research 17(22): 9193-9204.
Quartin, R. S., et al., 1989, Nucleic Acids Research 17(18): 7253-7262.
Stein, L. A., et al., 1988, Nucleic Acids Research 16(8): 3209-3221.

Primary Examiner—Robert A. Wax
Assistant Examiner—William W. Moore
Attorney, Agent, or Firm—Allegretti & Witcoff, Ltd.

[57] ABSTRACT

A method of site-directed alteration (removal or removal followed by replacement) of selected nucleotides in an RNA molecule, as well as to mixed phosphate backbone oligonucleotides useful in the method. It further relates to a method of producing polypeptides or proteins encoded by the RNA molecule altered by the present method. Through use of the present method, site-directed cleavage of an RNA molecule is effected, followed by excision of the selected or target segment of the RNA molecule.

12 Claims, No Drawings

METHOD OF SITE-SPECIFIC ALTERATION OF RNA AND PRODUCTION OF ENCODED POLYPEPTIDES

FUNDING

Work described herein was supported by the National Institutes of Health, the G. Harold and Leila Y. Mathers Foundation and the Worcester Foundation for Experimental Biology., This is a continuation of application Ser. No. 07/480.269, filed Feb. 15, 1990, now U.S. Pat. No. 5,149,797.

BACKGROUND

Several aspects of contemporary molecular genetics and biotechnology make it desirable to be able to produce genetically-altered proteins. For example, mutated protein domains are sometimes hyper-immunogenic, facilitating the production of neutralizing antibody-based vaccines. Moreover, site-directed mutations, ideally one amino acid at a time, can be a powerful approach to deciphering protein structure and/or enzyme-substrate reaction mechanisms.

Typically, deletions or substitutions of amino acids are made at the gene or DNA level, by recombinant DNA techniques which rely on the use of restriction endonucleases. However, restriction endonucleases available have a limited array of target sites in DNA (usually palindromic hexanucleotide or octanucleotide sequences). Deletion of a particular in-frame trinucleotide or trinucleotides may not be possible because there may be no suitably located restriction sites. As a result, presently-available methods of altering an amino acid sequence by altering the DNA sequence which encodes it, are limited in their applicability.

SUMMARY OF THE INVENTION

The present invention relates to a method of site-directed alteration (removal or removal followed by replacement) of selected nucleotides in an RNA molecule, as well as to mixed phosphate backbone oligonucleotides useful in the method. It further relates to a method of producing polypeptides or proteins encoded by the RNA molecule altered by the present method. Through use of the present method, site-directed cleavage of an RNA molecule is effected, followed by excision of the selected or target segment of the RNA molecule. Following cleavage and excision, in one embodiment, the two segments of the resulting interrupted RNA molecule are joined, through the action of an appropriate ligase. This results in production of a continuous RNA molecule, referred to as an altered RNA molecule, which is the same as the original RNA molecule except that it lacks the nucleotides originally present in the target segment of the RNA molecule. In a second embodiment, selected nucleotides can be introduced into the space or gap created by removal of the target RNA segment; a continuous RNA molecule is created by ligating the selected nucleotides introduced in this manner to the nucleotide on each side of the gap.

In the present method, an RNA molecule whose nucleotide sequence is to be altered in a site-directed manner is brought into contact with an oligonucleotide, referred to as a mixed phosphate backbone oligonucleotide, in the presence of RNase H. The mixed phosphate backbone oligonucleotide is complementary to all or a portion of an RNA molecule which includes a target segment to be altered. In addition, the mixed phosphate backbone oligonucleotide includes an internal portion or segment of deoxynucleotides which is capable of activating RNase H and is flanked on each side by a sequency of nucleotides which is unable to activate RNase H. The internal sequency includes two or more consecutive phosphodiester linkages, which may be unmodified or modified. The flanking sequences are modified deoxyribonucleotide or ribonucleotide sequences. It has been shown that when such a mixed phosphate backbone oligonucleotide is contacted with a target segment of an RNA molecule, according to the method of the present invention, the result is RNase H mediated excision of RNA target nucleotides complementary only to the internal sequence of oligonucleotides. This makes it possible to excise precisely any desired nucleotide or oligonucleotide from an RNA molecule. Followed by RNA ligation, this results in a desired altered messenger RNA or other type of RNA. Thus, for the first time, it is possible to carry out precise excision of a selected segment of an RNA molecule.

As a result, it is possible to selectively delete any desired number of nucleotides and, if desired, to introduce replacement nucleotides. The encoded amino acid sequency or polypeptide can be produced by expressing the altered RNA in vitro or in vivo. As a result, a selected amino acid sequence or selected polypeptide can be produced by the present method by: 1) producing an altered RNA molecule encoding a selected amino acid sequence or selected polypeptide and 2) expressing the altered RNA molecule under appropriate conditions. Cell-free translation of the altered RNA molecule can be carried out to produce desired mutant proteins useful, for example, for studies of protein structure or function. Alternatively, an appropriate mixed phosphate backbone oligonucleotide can be taken up by or introduced into cultured cells or into cells of an animal or a plant, in which endogenous RNase H and RNA ligase activities can produce altered RNAs; upon translation, corresponding genetically altered proteins are produced. This is useful, for example, as a means of producing defective viral or infectious/pathogenic agent replication or gene expression, which can be useful therapeutically or prophylactically.

DETAILED DESCRIPTION OF THE INVENTION

The present invention relates to a method of site-specific or site-directed alteration (removal or removal followed by replacement) of selected nucleotides (i.e., a target segment) in an RNA molecule, to produce an altered RNA sequence, as well as to mixed phosphate backbone oligonucleotides useful in the method. If further relates to a method of producing altered amino acid sequences or polypeptides by translating the altered RNA sequence, which results in production of the encoded molecule.

In the present method, a selected or target segment of an RNA molecule, such as pre-mRNA, mRNA or viral RNA, is altered as follows: an RNA molecule which includes the target segment (i.e., a nucleotide or a nucleotide sequence to be altered) is combined with an appropriately-selected mixed phosphate backbone oligonucleotide in the presence of RNase H. The mixed phosphate backbone oligonucleotide is complementary to all or a portion of the RNA molecule which includes the target RNA segment; it is of sufficient length to hybridize to the target RNA segment and sequences on either side and remain hybridized under the conditions used. The mixed phosphate backbone oligonucleotide has two key components: an internal portion or segment of deoxynucleotides which is capable of activating RNase H and two nucleotide sequences, which flank the internal segment, which are unable to activate RNase H. The internal deoxynucleotide segment includes two or more phosphodiester linkages, which may be unmodified or modified. The flanking nucleotide sequences may be deoxyribonucleotide or ribonucleotide sequences and is modified. That is, some or all of the internucleoside bridging phosphate residues are modified phosphates, such as methyl phosphonates, phosphoromorpholidates, phosphoropiperazidates and phosphoramidates. An essential feature of the mixed phosphate backbone oligonucleotide is that the internal complementary segment is RNase H activating and the flanking complementary sequences are unable to activate RNase H.

As demonstrated herein, site-directed alteration occurs when the RNA molecule which includes the target segment and an appropriately selected mixed phosphate backbone oligonucleotide are combined in the presence of RNase H and maintained under appropriate conditions (e.g., temperature, time, salt concentration) for complementary nucleotide sequences to hydridize and RNase H to be activated (i.e., to be able to cleave and excise). That is, as a result, the nucleotides in the RNA molecule to which the internal segment of the mixed phosphate backbone oligonucleotide is complementary are excised precisely from the RNA molecule.

In one embodiment of the present method, the gap resulting from excision of the target RNA segment can be closed by the activity of an appropriate ligase(s), resulting in a continuous RNA molecule referred to as an altered RNA molecule. The resulting altered RNA molecule differs from the RNA molecule only as to the target segment, which is not present in the altered RNA molecule.

In a second embodiment the gap created by the action of RNase H as described above can be filled in by introducing a segment of replacement nucleotides, which can be of any length appropriate to fit into the gap created in the RNA molecule. The segment of replacement nucleotides is subsequently linked to the adjacent nucleotides of the RNA molecule by an appropriately selected ligase(s). The nucleotide present at each end of the segment of replacement nucleotides is ligated to the nucleotide present on the respective "end" of the gas created in the RNA molecule. The resulting altered RNA molecule differs from the RNA molecule in that the target segment (present in the RNA molecule) has been removed and a replacement nucleotide sequence introduced in its place.

Altered RNA produced as described herein can be expressed, either in vitro or in vivo, to produce the encoded polypeptide or protein; as used herein, the term polypeptide includes proteins. For example, the altered RNA can be introduced into an appropriate vector, which is in turn introduced into a host cell capable of translating the altered RNA molecule and producing the encoded polypeptide. Polypeptides produced in this manner can be used for assessment of their structural/functional characteristics and a comparative assessment of polypeptides which differ in a defined manner (e.g., by selected amino acids). Such polypeptides can also be used therapeutically or prophylactically.

The following is a description of two embodiments of the present method of site-directed alteration of an RNA molecule: a first embodiment in which a selected nucleotide sequence (target segment) is removed and the resulting fragments ligated to produce an altered RNA molecule lacking the target segment and a second embodiment in which a selected nucleotide sequence is removed and replaced by a selected nucleotide or nucleotides, which are ligated to the nucleotide at each side of the gap created by removal of the target RNA segment.

Method for Excising a Specific Small Segment of Ribonucleotides from an RNA Molecule The RNA may be a pre-RNA, a viral RNA, or one of a variety of RNAs present in animal, plant or bacterial cells. A segment of DNA which is a mixed phosphate backbone oligodeoxynucleotide complementary to the RNA molecule can be synthesized using known techniques, such as chemical or enzymatic methods. The mixed phosphate backbone oligodeoxynucleotide includes an internal sequence which is capable of activating RNAse H and is flanked on each side by a DNA segment which is incapable of activating RNase H. The total length of the mixed phosphate backbone oligodeoxynucleotides varies, depending on the length of the target RNA segment to be altered, but must be sufficient to hybridize to the RNA molecule containing the target RNA segment and remain hybridized under the conditions used. The internal segment must be of sufficient length—at least two nucleotides—to be capable of activating RNase H, as demonstrated herein and by others (Walder, R. Y. and J. A. Walder, *Proc. Natl. acad. Sci. USA*, 85:5011–5015 (1988); Furdon, P. J. et al., *Nucleic Acids Res.*, 17:9193–9204 (1989)).

In the internal segment, the internucleoside bridging phosphate residues may be unmodified phosphates or any phosphate modification capable of activating RNase H, such as phosphorothioates. The flanking nucleotide sequences can be deoxyribonucleotides, as described in this embodiment or can be ribonucleotides and their modifications. The flanking sequences are connected by methyl phosphonates (PC), phosphoromorpholidates (PM), phosphoropiperazidates, phosphoramidates, or other modifications of internucleoside phosphates which are not able to activate RNase H. The RNA molecule and the modified backbone oligodeoxynucleotide are combined in the presence of RNase H, such as endogenous RNase H in a cell, and excision of the target segment occurs. A hairpin loop may form by pairing of complementary nucleotides, with the result that the two newly-formed segments are brought into proximity to each other. It may not be necessary that a hairpin loop form, however, in order for the segments produced by the activity of RNase H to be brought together because the two RNA segments are tethered by their base-pairing with the mixed phosphate backbone oligodeoxynucleotide. In the presence of an appropriate ligase(s), such as an endogenous ligase(s), the two newly-created segments are joined, by ligation of the nucleotide on each side of the gap.

The definition of "activating RNase H " is based on the induced-fit theory of Koshland, in which "enzyme sites were envisaged as somewhat flexible and undefined before binding occurred, locking active site residues into defined positions around the substrate" (Koshland, D. E., Jr., *Proc. Natl. Acad. Sci. USA*, 44:98 (1958);

Zeffren, E. and P. L. Hall, *The Study of Enzyme Mechanisms*, p. 201, John Wiley and Sons, New York, (1973)).

Method for Excising and Replacing a Specific Small Segment of Ribonucleotides from an RNA Molecule A second embodiment of the present invention may be useful, as described below, in repairing a genetic defect by removing the defective nucleotides and replacing them with others, such as those present in the normal RNA or those which result in RNA encoding a desired polypeptide. An RNA molecule to be altered, such as pre-mRNA or mRNA in which a defect is present, is combined with an appropriate mixed phosphate backbone oligodeoxyribonucleotide in which the internal segment is capable of activating RNase H and the flanking nucleotide sequences are unable to activate RNAse H, in the presence of RNase H. As described above, the target segment is excised in a site-directed manner, producing a split RNA molecule. In this embodiment, a replacemnt oligomer, which is the series of nucleotides to be inserted into the gap created by excision of the target segment, may be introduced into cells. Through hybridization exchange (as described in detail below), the replacemnt oligomer is introduced into the gap created as a result of the RNase H activity. Expression of the resulting altered RNA (which includes the desired/nondefective sequence is place of the defective sequence) may result in production of the desired/nondefective polypeptide.

Certain genetic disorders (inborn errors of metabolism) may be corrected by the method of the present invention. For example, cystic fibrosis is usually due to a gene mutation in which a specific phenylalanine codon is deleted (Riordon, J. R. et al., *Science*, 245: 1066–1073 (1989)). Through use of the present method, the mutant cystic fibrosis mRNA present in an individual's cells may be cleaved at the missing codon by site-directed RNase H alteration. Introduction into the individual's cells of the appropriate oligoribonucleotide (i.e., one encoding a phenylalanine), followed by endogenous RNA ligase activity may result in ligation and, thus, production of wild-type mRNA encoding a normal protein product.

Other genetic defects may be remedied in a similar manner. Examples of genetic defects for which this may be appropriate are: the substitution of serine for glycine 844 in a severe variant of osteogenesis imperfecta (Pack, M. et al., *J. Biol. Chem.*, 264:19694–19699 (1989)); a glycine to serine substitution in pro α (II) collagen in a form of dwarfism (Vissing, H. et al., *J. Biol. Chem.*, 264:18265–18267 (1989)); a glycine 833 conversion to aspartate in a mild variant of Ehlers-Danlos syndrome IV (Tromp, G. et al., *J. Biol. Chem.*, 264:19313–19317 (1989)); an A to G transition in an initiation codon mutation in the Apo C-II gene of a patient with a deficiency of apolipoprotein C-II (Fojo, S. S. et al., *J. Biol Chem.*, 264:10839–10842 ( 1989)); and an aberrant GT splice-donor signal flanking exon 19 in retinoblastoma RB-88 (Yandell, D. W. et al., *N.E. J. Med.*, 321:1689–1695 (1989)). Such precise genetic defects can be repaired at the BNA level by the method described.

Mode of Administration of Modified Backbone Oligonucleotide

The manner in which modified backbone oligonucleotides are provided will depend on the context in which they are used (i.e., in vitro, in vivo).

The modified backbone oligonucleotide is generally dissolved in water or a suitable buffered medium, such as Dulbecco's medium, Eagle's medium, or a similar physiological saline medium, typically at a concentration of $10^{-5}$ to $10^{-8}$ molar. In the case of a tissue culture system, the dissolved oligomer is sterilized by filtration through a bacterial filter, and is added to the other components of the tissue culture incubation medium. In the case of a seed, the oligomer is dissolved in water and added to the seeds spread on sterile filter paper inside a sterile covered glass or plastic dish. In the case of a plant, dissolved oligomer, in aqueous media, is added to the soil or other nutrient material in which the plant is growing. In the case of an animal or man, the oligomer, dissolved in physiological saline, may be injected subcutaneously, intraperitoneally, intramuscularly, intravenously, or possibly by capsule orally.

It has been shown that oligomers such as the above-described enter living cells, and are found in significant concentrations both in the cytoplasm and in the nucleus within minutes after administration (Zamecnik, P. C. et al., *Proc. Natl. Acad. Sci. USA*, 83:4143–4146 (1986); Goodchild, J . et., *Current Communications in Molecular Biology-Antisense RNA and DNA*, Cold Spring Harbor, pp. 135–139 (1 988); Wickstrom, E. L. et al., *Proc. Natl. Acad. Sci. USA*, 85:1028–1032 (1988)).

The following exemplification demonstrates that site-specific excision of nucleotides at the RNA level have been carried out, using the present method and modified backbone oligonucleotides as described herein.

EXEMPLIFICATION

Materials and Methods

Oligodeoxynucleotide Synthesis

Oligodeoxynucleotides were synthesized on an automated instrument (model 8700, Milligen, Mass.). Normal phosphodiester (PO) oligodeoxynucleotides and the analogous phosphorothioate (PS) or phosphoramidate oligodeoxynucleotides were synthesized using H-phosphonate chemistry (Agrawal, S. et al., *Proc. Natl. Acad. Sci. USA*, 86:7790–7794 ( 1989); and Agrawal, S. et al., *Proc. Natl. Acad. Sci. USA*, 85;7079–7083 (1 988)). Oligodeoxynucleoside methylphosphonate (PC) analogues were assembled by using nucleoside methylphosphonamidites (Agrawal, S. and J. Goodchild, *Tetrahedron Lett.*, 28: 3539–3542 (1987)). Oligodeoxynucleotides containing both PO and PC internucleoside linkages were assembled by using nucleoside-β-cyanoethyl phosphoramidites and nucleoside methylphosphonamidites, and oligodeoxynucleotides containing both PC and PS linkages were synthesized from nucleoside methylphosphonamidites (Agrawal. S. and J. Goodchild, *Tetrahedron Lett.*, 28:3539–3542 (1987)) and nucleoside H-phosphonates. Oligodeoxynucleotides containing both PO and phosphoramidate linkages were synthesized by using nucleoside-β-cyanoethylphosphoramidites and nucleoside H-phosphonates.

RNase H Assays

The 13-mer oligodeoxynucleotides complementary to nucleotides 2 -14 of human UI small nuclear RNA (counting the G cap as nucleotide (0)) were added at 100 μg/ml to a HeLa cell nuclear extract (Dignam, J. D. et al., *Nucleic Acids Res.*, 11:1475–1479 (1983)) containing 0.5 mM ATP, 20 mM creatine phosphate, 3.2 mM $MgCl_2$, and 1000 units of RNase per ml and were incubated under the conditions specified. RNA was isolated from the nuclear extract by phenol/chloroform extraction and ethanol precipitation, followed by electrophoresis in a 10% polyacrylamide gel containing 8.3 M urea. The RNAs were visualized by ethidium bromide staining.

A second RNase H assay was also carried out in nuclear extracts by using an exogenous $^{32}$P-labeled RNA. A 514-nucleotide test RNA (hereafter termed "514 RNA" for convenience) was generated by SP6 RNA polymerase transcription of a HindIII-linearized pGem-2 clone, pT7Hβ∆6. 514 RNA is antisense to the first two exons and intron of human β-globin pre-mRNA and was chosen for the reasons described below. 514 RNA labeled with a [α~$^{32}$P]GTP, [α~$^{32}$P]CTP, and [α~$^{32}$P]UTP was added to the nuclear extract containing the specified oligodeoxynucleotide at an oligomer-to-514 RNA molar ratio of 3000:1, unless otherwise noted. After incubation as specified, RNA was extracted and the $^{32}$P-labeled 514 RNA or its cleavage products were visualized by electrophoresis and autoradiography.

RESULTS

Action of RNase H on Oligodeoxynucleotide-U1 Small Nuclear RNA Hybrids

HeLa cell nuclear extracts contain RNase H activity that can act on DNA-RNA hybrids that form after addition of oligodeoxynucleotides complementary to certain endogenous nuclear RNAs (Krainer, A. R. and T. Maniatis, Cell, 42:725-736 (1985)). The ability of this RNase H activity to cleave the 5'-terminal nucleotides of endogenous U1 small nuclear RNA, after incubation of the various modified oligomers in the nuclear extract, was investigated. Incubation of the PO oligomer in the nuclear extract led to cleavage of a large proportion of the U1 RNA to a product (U1 *) having the mobility expected for removal of the first 15 nucleotides (cap, nucleotide 1, and nucleotides 2-14). There was a lack of effect on the mobility of any other RNAs present, demonstrating the high sequence specificity of the U1 oligomer-directed RNase H cleavage. U1 cleavage was also observed with the PS oligomer, although to a consistently lesser extent than with the PO oligomer. In contrast, no cleavage was observed with the PC, phosphoroN-morpholidate (PM), or phosphoro-N-butylamidate (PB) oligomers. Reducing the temperature of incubation to 20° C. and extending the time to 60 minutes did not increase the extent of cleavage observed with the PS oligomer, nor did it reveal cleavages with the PC, PM and PB oligomers. The pattern of U1 cleavages seen with the various oligomers was also not altered by adding E. coli RNase H (Pharmacia, final concentration 8 units/ml) to the nuclear extract at the outset of incubation.

RNase H Action at an Internal RNA Site Hybridized with Normal and Modified Oligodeoxynucleotides The foregoing U1 RNA cleavages involve the 5' extremity of a small RNA. Indeed, the 5' end of U1 RNA is an exceptionally favored target for oligodeoxynucleotide-directed RNase H cleavage since almost all the other regions of this RNA molecule are tightly complexed with proteins in the U1 small nuclear ribonucleoprotein particle (Patton, J. R. et al., Mol. Cell. Biol., 7: 4030-4037 (1987); Patton, J. R. et al., Proc. Natl. Acad. Sci. USA, 85:747-751 (1988); Patton, J. R. et al., Mol. Cell. Biol., 9:3360-3368 (1989)). Therefore, the action of RNase H on hybrids formed by normal or modified oligomers at internal sites in a longer RNA was also investigated.

For this purpose a test RNA which is 514 nucleotides long (termed 514 RNA) was used. 514 RNA is antisense to the first two exons and intron of human β-globin pre-mRNA. The underlying reasoning was that, because it is antisense to a pre-mRNA, 514 RNA would not undergo splicing when added to nuclear extract (the cleavage-ligation steps of which would otherwise complicate analysis of oligodeoxynucleotide-directed RNase H cleavages).

A series of normal and modified 15-mer oligodeoxynucleotides complementary to nucleotides 349-363 of 514 RNA was synthesized chemically (Table 1, oligomers A-E). This particular 514 RNA site was selected because oligomer-directed RNase H cleavage would generate two fragments of readily distinguishable lengths (150 and 348 nucleotides) and also because this 15-nucleotide sequence does not occur elsewhere in 514 RNA (Lawn, R. M. et a.., Cell, 21:647-651 (1980)). Melting curves in 0.16 M Na+ for four of these oligodeoxynucleotides after duplex formation with the complementary (PO) oligomer revealed that the PO, PC, PS and PM oligomer-containing duplexes had $t_m$s of 53° C., 46° C., 43° C. and 38+ C., respectively, indicating a lower duplex stability for the modified oligomers, in part confirming previous reports (Stein, C. A. et al., Nucleic Acids Res., 16:3209-3221 (1988); Froehler, B. et al., Nucleic Acids Res., 16:4831-4839 (1988); Quartin, R. S. and J. G. Wetmur, Biochemistry, 28:1040-1047 (1989); Agrawal. S. et al., Nucleosides Nucleotides, 8:819-823 (1989)).

TABLE 1

| Oligomer | Sequence | | | | | Internucleoside Linkage |
|---|---|---|---|---|---|---|
| A | GTA | TCA | AGG | TTA | CAA | PO |
| B | GTA | TCA | AGG | TTA | CAA | PS |
| C | GTA | TCA | AGG | TTA | CAA | PM |
| D | GTA | TCA | AGG | TTA | CAA | PB |
| E | GTA | TCA | AGG | TTA | CAA | PC |
| F* | GTA | TCA | TAT | GAG | ACA | PO |
| G* | GTA | GCA | AGG | CTA | CAA | PO |
| H* | GTA | TGA | GAC | ATA | TAC | PO |

Underlined nucleotides indicate base pairing mismatches; PB is phospho-N-butylamidate.

The series of normal and modified oligodeoxynucleotides shown in Table 1 were incubated with $^{32}$P-labeled 514 RNA in nuclear extracts, under the conditions specified in the Materials and Methods section, for either 30 minutes or 3.5 hours.

The results of incubating these oligomers with 514 RNA in HeLa nuclear extract are as follows: After 30 minutes of incubation without any oligomer, intact input 514 RNA was the only labeled species visualized. After 3.5 hours of incubation without any oligomer, the 514 RNA was completely degraded by the action of ribonuclease known to be present in the extract. Incubation of 514 RNA in the extract for 30 minutes together with either the PO or PS oligomers resulted in precise cleavage of the substrate RNA into two fragments of the sizes expected from the location of the oligomer-complementary sequence. Surprisingly, in the case of the PS oligomer, these two fragments were still present, albeit in slightly degraded form, after 3.5 hours of incubation. Incubation of 514 RNA with PM oligomer for 30 minutes resulted in partial cleavage. This partial cleavage is due to the presence of contaminating unmodified oligomer in the experiment. No cleavage was observed with the PB or PC oligomers under these conditions.

PO oligomers that were only partially complementary to 514 RNA (oligomers F, G and H in Table 1) were also tested. None of these oligomers, containing 4, 5 or 6 uninterrupted complementary nucleotides out of the 15 (Table 1), elicited RNase H cleavage of 514 RNA.

The finding that the PS oligomer was less effective than the PO oligomer in eliciting RNase H cleavage in the U1 RNA assay raised the possibility that the more complete RNase H cleavages observed with both PO and PS oligomers in the 514 RNA assay might reflect the particular reaction conditions employed. Therefore, a range of oligomer-to-514 RNA molar ratios tests (0.1:1-1000:1), all below that used in the above-described (3000:1), was investigated. Results showed that virtually complete 514 RNA cleavage occurred with the PO oligomer at an oligomer-to-RNA ratio of 100:1, whereas a comparable extend of 514 cleavage with the PS oligomer occurred at a oligomer-to-TNA ratio of 1000:1. A very similar, incomplete extent of cleavage was observed with the PO and PS oligomers at ratios of 10:1 and 100:1, respectively. The possibility that these results might reflect a preferential instability of the PS oligomer during incubation in the nuclear extracts was examined by experiments in which either the PO or the PS oligomer was preincubated in nuclear extract for 30 minutes, followed by addition of $^{32}$P-labeled 514 RNA and incubation for an additional 30 min. This revealed the same extent of difference in RNAse H cleavage as described above.

"Restriction Endonuclease-Like" Cleavage with Oligomers Containing RNase H-Sensitive and -Resistant Internucleoside Linkages The extreme difference between the RNase H sensitivity of DNA-RNA hybrids containing PO or PS oligodeoxynucleotides, contrasted with ones with PC, PM or PB oligomers, led to an investigation of how RNase H acts on a DNA-RNA hybrid in which only a small proportion of internucleoside linkages in the DNA strand were RNase H-sensitive. Table 2 shows the series of oligomers that were synthesized to address this issue.

TABLE 2

| Oligomer | Sequence |
|---|---|
| I | AGG T |
| J | A AGG TT |
| K | GTA TCA AGG TTA CAA |
| L | GTA TCA AGG TTA CAA |
| M | GTA TCA AGG TTA CAA |
| N | GTA TCA AGG TTA CAA |
| O | GTA TCA AGG TTA CAA |
| P | GTA TCA AGG TTA CAA |
| Q | GTA TCA AGG TTA CAA |
| R | GTA TCA AGG TTA CAA |

Underlined nucleotides are PC; dashed nucleotides are PS; Boxed nucleotides are phosphoromorpholidates; Double-underlined nucleotides are PM (oligomer Q) or PB; the remaining nucleotides are PO.

The oligomers listed were tested for their capacity to elicit RNase H action after hybridization to 514 RNA, as in the preceding experiments.

Results demonstrated that neither a tetramer nor a hexamer (all PO) oligodeoxynucleotide complementary to 514 RNA was able to induce RNase H cleavage in this nuclear extract system. When PO/PC-containing pentadecamers containing either two or four consecutive PO linkages were used, a low but readily detectable level of RNase H cleavage occurred. In contrast, a pentadecamer containing six consecutive PO linkages elicited complete RNase H cleavage of the substrate RNA. Note that the six PO nucleotides in this oligomer (oligomer M in Table 2) are identical in sequence to the RNase H-inactive hexamer (oligomer J), from which it is inferred that the potency of the pentadecamer reflects its increased hybrid stability with 514 RNA owing to the additional nine complementary nucleotides.

Similar tests were performed with mixed PO/PC pentadecamers complementary to a different site in 514 RNA (i.e., nucleotides 463-477). These tests revealed an effect of the number of PO linkages on RNase H cleavage similar to that described above.

Additional variants of mixed PO/PC oligomers were also tested. Pentadecamer PO/PC oligomers with five or six consecutive PO linkages at either the extreme 5' or 3' and were highly effective in eliciting RNase H cleavage. A PS/PC pentadecamer with six consecutive PS linkages at the extreme 5' end (oligomer P in Table 2) was only partially active. Comparison of these results with lanes 2 and 3 in FIG. 4B confirms the above-described results showing that all-PS oligomers are less effective than all-PO oligomers in eliciting RNase H cleavage. RNase H cleavage of 514 RNA was also observed with a 15-mer containing nine consecutive PM or PB linkages followed by six PO-linked nucleotides (oligomers Q and R in Table 2).

EQUIVALENTS

Those skilled in the art will recognize, or be able to ascertain, using no more than routine experimentation, many equivalents to the specific embodiments of the invention described specifically herein. Such equivalents are intended to be encompassed by the scope of the following claims.

We claim:

1. A mixed phosphate backbone oligonucleotide comprising a 5' segment of nucleotides that activate RNase H and a 3' segment of nucleotides that do not activate RNase H, wherein the 5' segment of nucleotides comprises nucleotide phosphodiesters and wherein the 3' segment of nucleotides comprises two or more contiguous nucleotide alkylphosphonates.

2. A mixed phosphate backbone oligonucleotide comprising a 5' segment of nucleotides that activate RNase and a 3' segment of nucleotides that do not activate Rnase H, wherein the 5' segment of nucleotides comprises nucleotide phosphodiesters and wherein the 3' segment of nucleotides comprises nucleotide phosphoromorpholidates.

3. A mixed phosphate backbone oligonucleotide comprising a 5' segment of nucleotides that activate RNase and a 3' segment of nucleotides that do not activate Rnase H, wherein the 5' segment of nucleotides comprises nucleotide phosphodiesters and wherein the 3' segment of nucleotides comprises nucleotide phosphoramidates.

4. A mixed phosphate backbone oligonucleotide comprising a 5' segment of nucleotides that do not activate RNase H and a 3' segment of nucleotides that activate RNase H wherein the 5' segment of nucleotides comprises three or more contiguous nucleotide alkylphosphonates and the 3' segment of nucleotides comprises nucleotide phosphodiesters.

5. A mixed phosphate backbone oligonucleotide comprising a 5' segment of nucleotides that do not activate RNase H and a 3' segment of nucleotides that activate RNase H wherein the 5' segment of nucleotides comprises nucleotide phosphoromorpholidates and the 3' segment of nucleotides comprises nucleotide phosphodiesters.

6. A mixed phosphate backbone oligonucleotide comprising a 5' segment of nucleotides that do not activate RNase H and a 3' segment of nucleotides that activate RNase H wherein the 5' segment of nucleotides comprises nucleotide phosphoramidates and the 3' segment of nucleotides comprises nucleotide phosphodiesters.

7. A mixed phosphate backbone oligonucleotide comprising a 5' segment of nucleotides that activate RNase and a 3' segment of nucleotides that do not activate RNase H, wherein the 5' segment of nucleotides comprises nucleotide phosphorothioates and wherein the 3' segment of nucleotides comprises nucleotide alkylphosphonates.

8. A mixed phosphate backbone oligonucleotide comprising a 5' segment of nucleotides that activate RNase and a 3' segment of nucleotides that do not activate RNase H, wherein the 5' segment of nucleotides comprises nucleotide phosphorothioates and wherein the 3' segment of nucleotides comprises nucleotide phosphoromorpholidates.

9. A mixed phosphate backbone oligonucleotide comprising a 5' segment of nucleotides that activate RNase and a 3' segment of nucleotides that do not activate RNase H, wherein the 5' segment of nucleotides comprises nucleotide phosphorothioates and wherein the 3' segment of nucleotides comprises nucleotide phosphoramidates.

10. A mixed phosphate backbone oligonucleotide comprising a 5' segment of nucleotides that do not activate RNase H and a 3' segment of nucleotides that activate RNase H wherein the 5' segment of nucleotides comprises nucleotide alkylphosphonates and the 3' segment of nucleotides comprises nucleotide phosphorothioates.

11. A mixed phosphate backbone oligonucleotide comprising a 5' segment of nucleotides that do not activate RNase H and a 3' segment of nucleotides that activate RNase H wherein the 5' segment of nucleotides comprises nucleotide phosphoromorpholidates and the 3' segment of nucleotides comprises nucleotide phosphorothioates.

12. A mixed phosphate backbone oligonucleotide comprising a 5' segment of nucleotides that do not activate RNase H and a 3' segment of nucleotides that activate RNase H wherein the 5' segment of nucleotides comprises nucleotide phosphoramidates and the 3' segment of nucleotides comprises nucleotide phosphorothioates.

* * * * *

UNITED STATES PATENT AND TRADEMARK OFFICE
CERTIFICATE OF CORRECTION

PATENT NO. : 5,220,007
DATED : June 15, 1993
INVENTOR(S) : Pederson et al.

It is certified that error appears in the above-indentified patent and that said Letters Patent is hereby corrected as shown below:

Column 1, delete lines 7-10 and insert the following therefor

--This invention was made with support from the G. Harold and Leila Y. Mathers Foundation, the Worcester Foundation for Experimental Biology, and the government under grant numbers Al-24846-03 and GM-21595-15 from the National Institutes of Health. The government has certain rights in this invention.--

Signed and Sealed this

Thirtieth Day of August, 1994

BRUCE LEHMAN

Attest:

Attesting Officer

*Commissioner of Patents and Trademarks*